United States Patent
Zhou et al.

(10) Patent No.: US 10,513,578 B2
(45) Date of Patent: Dec. 24, 2019

(54) ETHERAMINES AND THEIR USE AS CURATIVES OR INTERMEDIATES FOR POLYMER SYNTHESIS

(71) Applicant: Huntsman Petrochemical LLC, The Woodlands, TX (US)

(72) Inventors: Hui Zhou, The Woodlands, TX (US); David C Lewis, Conroe, TX (US); Howard P Klein, Austin, TX (US); Terry L Renken, Conroe, TX (US); Leah Patterson, The Woodlands, TX (US)

(73) Assignee: HUNTSMAN Petrochemical LLC, The Woodlands, TX (US)

( * ) Notice: Subject to any disclaimer, the term of this patent is extended or adjusted under 35 U.S.C. 154(b) by 0 days.

(21) Appl. No.: 15/033,704

(22) PCT Filed: Oct. 30, 2014

(86) PCT No.: PCT/US2014/063054
§ 371 (c)(1),
(2) Date: May 2, 2016

(87) PCT Pub. No.: WO2015/069531
PCT Pub. Date: May 14, 2015

(65) Prior Publication Data
US 2016/0257778 A1    Sep. 8, 2016

Related U.S. Application Data

(60) Provisional application No. 61/900,117, filed on Nov. 5, 2013.

(51) Int. Cl.
C07C 213/02    (2006.01)
C07C 217/42    (2006.01)
C08G 59/50    (2006.01)
C08G 18/50    (2006.01)

(52) U.S. Cl.
CPC .......... *C08G 59/504* (2013.01); *C07C 213/02* (2013.01); *C07C 217/42* (2013.01); *C08G 18/5024* (2013.01)

(58) Field of Classification Search
CPC .................................................... C07C 217/42
See application file for complete search history.

(56) References Cited

U.S. PATENT DOCUMENTS

| | | |
|---|---|---|
| 2,683,730 A | 7/1954 | Fauser et al. |
| 2,950,263 A | 8/1960 | Herbert et al. |
| 3,012,008 A | 12/1961 | Lister |
| 3,152,998 A | 10/1964 | Moss |
| 3,344,162 A | 9/1967 | Rowton |
| 3,362,979 A | 1/1968 | Bentley |
| 3,394,164 A | 7/1968 | Kolakowski et al. |
| 3,654,370 A | 4/1972 | Yeakey |
| 4,152,353 A | 5/1979 | Habermann |
| 4,705,814 A | 11/1987 | Grigsby, Jr. et al. |
| 4,748,192 A | 5/1988 | Smith |
| 4,766,245 A | 8/1988 | Larkin et al. |
| 4,769,438 A | 9/1988 | Zimmerman et al. |
| 5,639,413 A | 6/1997 | Crivello |
| 5,912,189 A | 6/1999 | Wolak et al. |
| 5,972,563 A | 10/1999 | Steinmann et al. |
| 6,060,625 A | 5/2000 | Su et al. |
| 7,550,550 B2 | 6/2009 | Klein et al. |
| 9,054,313 B2 | 6/2015 | Klein et al. |
| 2005/0234216 A1* | 10/2005 | Klein .................. C07C 217/42 528/422 |
| 2010/0159228 A1* | 6/2010 | Smith .................. C08G 18/324 428/292.1 |
| 2010/0240860 A1 | 9/2010 | Abraham et al. |
| 2012/0071623 A1 | 3/2012 | Eling et al. |

(Continued)

FOREIGN PATENT DOCUMENTS

| | | |
|---|---|---|
| WO | 2000/66538 A | 11/2000 |
| WO | 2011/079125 A | 6/2011 |
| WO | 2012/149340 A | 11/2012 |

OTHER PUBLICATIONS

ChemBook entry for glycerol, no date.*

(Continued)

*Primary Examiner* — David J Buttner
(74) *Attorney, Agent, or Firm* — Huntsman Petrochemical LLC; Lewis Craft

(57) ABSTRACT

Implementations described herein generally relate to etheramine mixtures formed from a mixture of two or more multifunctional alcohol initiators, processes for the etheramine mixtures production, and its use as a curing agent or as a raw material in the synthesis of polymers. In one implementation, the process comprises mixing a polyol initiator having a melting point greater than a processing temperature and a polyol initiator having a melting point less than the processing temperature to form a polyol initiator mixture having a melting point less than the processing temperature, charging the polyol initiator mixture to an alkoxylation reaction zone, contacting the polyol initiator mixture with an alkylene oxide in the alkoxylation reaction zone to provide a mixture of alkoxylated precursor polyols and charging the mixture of alkoxylated precursor polyols to a reductive amination zone and reductively aminating the mixture of alkoxylated precursor polyols to form the etheramine mixture.

10 Claims, No Drawings

(56) References Cited

U.S. PATENT DOCUMENTS

2012/0259075 A1 10/2012 Klein et al.
2012/0283405 A1 11/2012 Klein et al.

OTHER PUBLICATIONS

ChemBook entry for ethylene glycol, no date.*
ChemBook entry for 1,3 propane diol, no date.*
ChemBook entry for propylene glycol, no date.*
The Merck Index; entry for neopentyl glycol (1977) p. 840. (Year: 1977).*
ChemBook entry for 1,3 Butanediol. No date (Year: 0000).*

* cited by examiner

ETHERAMINES AND THEIR USE AS CURATIVES OR INTERMEDIATES FOR POLYMER SYNTHESIS

CROSS-REFERENCE TO RELATED APPLICATIONS

This application is the National Phase of International Application PCT/US2014/063054 filed Oct. 30, 2014 which designated the U.S. and which claims priority to U.S. App. Ser. No. 61/900,117 filed Nov. 5, 2013. The noted applications are incorporated herein by reference.

BACKGROUND

Field

Implementations described herein generally relate to etheramine mixtures formed from a mixture of two or more multifunctional alcohol initiators, processes for the etheramine mixtures production, and its use as a curing agent or as a raw material in the synthesis of polymers.

Description of the Related Art

Polyoxyalkylene amines, or "polyetheramines" as they are sometimes called, are useful as curing agents in epoxy systems to improve flexibility, and to lengthen working time in the manufacture of fiber-reinforced composites. Polyetheramines are generally produced by the reaction of an alkylene oxide with an alcohol to form a polyoxyalkylene polyol and then the hydroxyl groups are subsequently converted to amine groups by reductive amination. For example U.S. Pat. No. 3,654,370 describes a process in which a polyoxyalkylene polyol is treated with ammonia and hydrogen in the presence of a nickel oxide, copper oxide and chromium oxide catalyst to form a mixture of polyether amines. U.S. Pat. No. 4,766,245 further describes a process in which high molecular weight polyoxyalkylene amines are produced by contacting high molecular weight polyoxyalkylene polyols with ammonia in the presence of hydrogen and a Raney nickel/aluminum catalyst. Additionally, U.S. Pat. No. 4,769,438 describes a process in which a propoxylated 1,4-butanediol is first aminated using a Raney nickel catalyst and then subsequently converted to an adduct by a reaction with a small amount of an epoxy resin. Finally, U.S. Pat. No. 7,550,550 describes a process for producing hindered polyetherdiamines and polyethertriamines by reductive amination of a variety of polyoxyalkylene polyols.

In some processes for producing polyetheramines, the alcohol precursors used for alkoxylation are typically liquids at room temperature or low melting point solid raw materials. Due to high energy consumption and requirement of more capital investment to add heat tracing capability, higher melting point raw materials are typically excluded from current processes. These high melting point raw materials, sometimes have unique features, such as, rigid backbone, high functionality etc.

Therefore, there is a need for improved processes for producing etheramine mixtures from two or more multifunctional alcohol initiators wherein at least one of the multifunctional initiators is a higher melting point alcohol.

SUMMARY

Implementations described herein generally relate to etheramine mixtures formed from a mixture of two or more multifunctional alcohol initiators, processes for the etheramine mixtures production, and its use as a curing agent or as a raw material in the synthesis of polymers. In one implementation, a process for preparing an etheramine mixture is provided. The process comprises (a) mixing a first polyol initiator having a melting point greater than a processing temperature and a second polyol initiator having a melting point less than the processing temperature to form a polyol initiator mixture having a melting point less than the processing temperature, (b) charging the polyol initiator mixture to an alkoxylation reaction zone in the presence of an alkali metal hydroxide catalyst, (c) contacting the polyol initiator mixture with an alkylene oxide in the alkoxylation reaction zone to provide a mixture of alkoxylated precursor polyols and (d) charging the mixture of alkoxylated precursor polyols to a reductive amination zone and reductively aminating the mixture of alkoxylated precursor polyols in the presence of a reductive amination catalyst and ammonia to form the etheramine mixture.

In another implementation, a composition comprising an etheramine mixture is provided. The etheramine mixture comprises the reaction product of ammonia and a mixture of alkoxylated precursor polyols, wherein the reaction is conducted under reductive amination reaction conditions, wherein the mixture of alkoxylated polyols is the reaction product of a polyol initiator mixture having a melting point less than a processing temperature with an alkylene oxide and wherein the polyol initiator mixture comprises a first polyol initiator having a melting point greater than the processing temperature and a second polyol initiator having a melting point less than the processing temperature.

In yet another implementation, a composition is provided. The composition comprises:

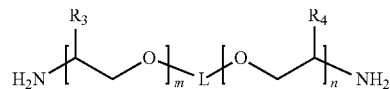

wherein L is a linear or branched $C_2$-$C_{18}$ alkylene, preferably $C_2$-$C_{12}$ alkylene and particularly preferably $C_2$-$C_6$ alkylene; $C_3$-$C_{12}$ cycloalkylene, preferably $C_4$-$C_8$ cycloalkylene and particularly preferably $C_5$-$C_8$ cycloalkylene; $C_2$-$C_4$ alkylene-$C_3$-$C_{12}$ cycloalkylene and preferably $C_2$-$C_4$ alkylene-$C_5$-$C_6$ cycloalkylene; $C_2$-$C_4$ alkylene-$C_3$-$C_{12}$ cycloalkylene-$C_2$-$C_4$ alkylene and preferably $C_2$-$C_4$ alkylene-$C_5$-$C_6$ cycloalkylene-$C_2$-$C_4$ alkylene, wherein $R_3$ and $R_4$ may be identical or different and may each be, independently of one another, hydrogen, a linear or branched $C_1$ to $C_5$ alkyl group, a linear or branched $C_2$-$C_5$ alkenyl group, or a substituted or unsubstituted $C_6$-$C_{12}$ aryl group and wherein m and n may each individually be a number from 0 to 6 wherein at least one of m and n is 1 or more.

In yet another implementation, a composition is provided. The composition comprises:

wherein $R_5$ and $R_6$ are identical or different and are each, independently of one another, hydrogen, a linear or branched $C_1$ to $C_5$ alkyl group, a linear or branched $C_2$-$C_5$ alkenyl group, or a substituted or unsubstituted $C_6$-$C_{12}$ aryl group and m+n equals a non-zero whole number between one and six.

DETAILED DESCRIPTION

Implementations described herein generally relate to etheramine mixtures formed from a mixture of two or more multifunctional alcohol initiators, processes for the etheramine mixtures production, and its use as a curing agent or as a raw material in the synthesis of polymers. More particularly, the implementations described herein generally relate to etheramine mixtures formed from at least two multifunctional alcohol initiators where at least one of the initiators is a high melting point polyol.

Some implementations described herein further relate to the synthesis of amine-terminated compounds from a mixture of two or more multifunctional alcohol initiators with an alkylene oxide (e.g., ethylene oxide (EO), propylene oxide (PO) or butylene oxide (BO)), followed by further reductive amination. The amine-terminated compounds may be used to produce products having improved thermal stability, enhanced glass transition temperature and in some implementations having slower amine reactivity. Such products are useful in curing epoxy composite binders, especially those used in the manufacture of wind turbine generator blades. The implementations described herein further provide several processing approaches to prepare the above material compositions.

The implementations described herein further include the synthesis of new compositions of matter, which are etheramines having significant quantities of oligomers with only limited amounts of oxygen atoms in the oligomer backbone. Some implementations described herein further provide enhanced thermal stability and retardance of amine reactivity which makes possible epoxy systems with greatly improved thermal resistance, as measured by glass transition temperatures, when used to cure epoxy resins and long open time for large size of blade application.

In some implementations, in order to produce such etheramines, alkylene oxides are adducted to a mixture of two or more multifunctional alcohol initiators to form a mixture of alkoxylated polyols. These intermediate polyols are then subjected to reductive amination. The crude reaction products may then be stripped of ammonia and water to provide the final mixture of amine products, which may then be analyzed for amine conversions, water content and oligomer mixture ratios.

Using the implementations described herein, high yields of polyfunctional amines having low color and viscosity, containing rigid and hindered structure in molecules may be produced. Suitable multifunctional alcohol based initiators include but are not limited to neopentyl glycol, 1,4-cyclohexanedimethanol, 1,4-butanediol, ethylene glycol and combinations thereof.

These mixtures of polyfunctional amines described herein may be used as intermediates in a number of polymer-forming applications. These mixtures may also find use as components of epoxy curatives to provide high thermal stability to structural composites or molded materials. These mixtures may also be useful in adhesives and coatings for various industrial materials. Some of these products may be used to prepare polyurea and thermoplastic polyamide materials.

In some implementations, a process for preparing an etheramine mixture as described herein is provided. The process comprises (a) mixing a first polyol initiator having a melting point greater than a processing temperature and a second polyol initiator having a melting point less than the processing temperature to form a polyol initiator mixture having a melting point less than the processing temperature, (b) charging the polyol initiator mixture to an alkoxylation reaction zone in the presence of an alkali metal hydroxide catalyst, (c) contacting the polyol initiator mixture with an alkylene oxide in the alkoxylation reaction zone to provide a mixture of alkoxylated precursor polyols and (d) charging the mixture of alkoxylated precursor polyols to a reductive amination zone and reductively aminating the mixture of alkoxylated precursor polyols in the presence of a reductive amination catalyst and ammonia to form the etheramine mixture.

In some implementations, a first polyol initiator having a melting point greater than a processing temperature is mixed with a second polyol initiator having a melting point less than the processing temperature to form a polyol initiator mixture having a melting point less than a processing temperature. The first polyol initiator may be a high melting point initiator. The first polyol initiator may be a solid, semi-solid or a combination thereof at processing temperatures. The second polyol initiator may be a low melting point initiator. The second polyol initiator may be liquid at processing temperatures. The first polyol initiator and the second polyol initiator may each individually be a diol. The first polyol initiator and the second polyol initiator may each be individually selected from a polyol based on formula (I):

In formula (I) L may be a linear or branched $C_2$-$C_{18}$ alkylene, preferably $C_2$-$C_{12}$ alkylene and particularly preferably $C_2$-$C_6$ alkylene; $C_3$-$C_{12}$ cycloalkylene, preferably $C_4$-$C_8$ cycloalkylene and particularly preferably $C_5$-$C_8$ cycloalkylene; $C_2$-$C_4$ alkylene-$C_3$-$C_{12}$ cycloalkylene and preferably $C_2$-$C_4$ alkylene-$C_5$-$C_6$ cycloalkylene; $C_2$-$C_4$ alkylene-$C_3$-$C_{12}$ cycloalkylene-$C_2$-$C_4$ alkylene and preferably $C_2$-$C_4$ alkylene-$C_5$-$C_6$ cycloalkylene-$C_2$-$C_4$ alkylene.

The first polyol initiator may include polyol initiators that are solid or semi-solid at processing temperatures. Suitable first polyol initiators include neopentyl glycol. The first polyol initiator may have a melting point greater than 60° C., greater than 70° C., greater than 80° C., greater than 90° C., greater than 100° C., greater than 110° C., greater than 120° C. and greater than 130° C.

The second polyol initiator may be a liquid or semi-solid at processing temperatures. Suitable second polyol initiators include but are not limited to 1,4-cyclohexanedimethanol, 1,4-butanediol, ethylene glycol, 1,3-propanediol, 2-methyl-1,3-propanediol, 2,2,4-trimethyl-1,3-pentanediol, hexanediol, trimethylolpropane, triethylolpropane, pentraerythritol, cyclobutanediol, cyclopentanediol, cyclohexanediol, cyclododecanediol and combinations thereof. The second polyol initiator typically has a melting point less than the melting point of the first polyol initiator. The second polyol initiator may have a melting point less than 100° C., less than 90° C., less than 80° C., less than 70° C., less than 60° C., less than 50° C., less than 40° C., less than 30° C., less than 20° C., less than 10° C. and less than 0° C.

In some implementations, the melting point of the second polyol initiator mixture is less than 60° C. and the melting point of the first polyol initiator is greater than 60° C.

In some implementations, the weight ratio of first polyol initiator to second polyol initiator in the polyol initiator mixture is from about 10:90 to about 90:10.

After charging, the polyol initiator mixture to an alkoxylation reaction zone, the polyol initiator mixture is then contacted with an alkylene oxide in the alkoxylation reaction zone for a period of time sufficient to provide a mixture of alkoxylated polyols The alkylene oxide may be an alkylene oxide having the formula (II):

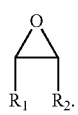
(II)

In formula (II), $R_1$ and $R_2$ may be identical or different and each may be, independently of one another, hydrogen, a linear or branched $C_1$-$C_6$ alkyl group, a linear or branched $C_2$-$C_5$ alkenyl group, or a substituted or unsubstituted $C_6$-$C_{12}$ aryl group. Preferably, the alkylene oxide is ethylene oxide, propylene oxide, butylene oxide (such as isobutylene oxide, 1,2-butylene oxide, and 2,3-butylene oxide), pentylene oxide, styrene oxide or a combination thereof. The amount of alkylene oxide which is contacted with the mixture of polyol initiators may range from about 0 to 5 moles, preferably from about 0.5 to 2 moles of alkylene oxide per mole of polyol initiator. The period of time the initiator is contacted with the alkylene oxide is a period of time sufficient to form a mixture of alkoxylated polyols and in some implementations may range from about 0.5 hours to about 24 hours.

In one implementation, the alkoxylation reaction zone is a closed reaction vessel and alkoxylation is carried out under elevated temperature and pressure and in the presence of a base catalyst. Thus, alkoxylation may be conducted at a processing temperature ranging from about 50° C. to about 150° C. The processing temperature may be greater than 50° C., greater than 60° C., greater than 70° C., greater than 80° C., greater than 90° C., greater than 100° C., greater than 110° C., greater than 120° C., greater than 130° C., greater than 140° C. or greater than 150° C. Alkoxylation may be conducted at a pressure ranging from about 40 psi to about 100 psi. The base catalyst may be any alkaline compound customarily used for base-catalyzed reactions, for example, an alkali metal hydroxide such as sodium hydroxide, lithium hydroxide, potassium hydroxide, or cesium hydroxide, or a tertiary amine, such as dimethyl cyclohexylamine or 1,1,3,3-tetramethylguanidine. After alkoxylation, unreacted oxide may be stripped out, and the resulting mixture may be neutralized with magnesium silicate (i.e., Magnesol®). The reaction mixture may then be stripped to remove any light reactants and water and then the filtered alkoxylated polyols may be collected.

The mixture of alkoxylated polyols may include at least one alkoxylated polyol based on formula (III):

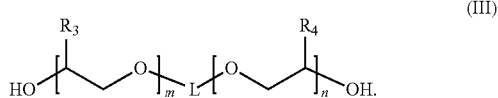
(III)

In formula (III) $R_3$ and $R_4$ may be identical or different and may each be, independently of one another, hydrogen, a linear or branched $C_1$ to $C_5$ alkyl group, a linear or branched $C_2$-$C_5$ alkenyl group, or a substituted or unsubstituted $C_6$-$C_{12}$ aryl group, such as $CH_3$, $C_2H_5$ or $C_6H_5$. m and n may each individually be a number from 0 to 6, for example, 0, 1, 2, 3, 4, 5 or 6, wherein at least one of m and n is 1 or more. m+n may be a number between 1 and 12, for example, 1, 2, 3, 4, 5, 6, 7, 8, 9, 10, 11 or 12. L may be a linear or branched $C_2$-$C_{18}$ alkylene, preferably $C_2$-$C_{12}$ alkylene and particularly preferably $C_2$-$C_6$ alkylene; $C_3$-$C_{12}$ cycloalkylene, preferably $C_4$-$C_8$ cycloalkylene and particularly preferably $C_5$-$C_8$ cycloalkylene; $C_2$-$C_4$ alkylene-$C_3$-$C_{12}$ cycloalkylene and preferably $C_2$-$C_4$ alkylene-$C_5$-$C_6$ cycloalkylene; $C_2$-$C_4$ alkylene-$C_3$-$C_{12}$ cycloalkylene-$C_2$-$C_4$ alkylene and preferably $C_2$-$C_4$ alkylene-$C_5$-$C_6$ cycloalkylene-$C_2$-$C_4$ alkylene.

The mixture of alkoxylated polyols may then be used as a feedstock for the reductive animation step. Because the addition during alkoxylation is random, the mixture of alkoxylated polyols formed in the alkoxylation reaction zone will not be a pure compound, but rather will be a mixture of unreacted initiator and monoether and polyether polyols. The proportion of these polyols can be varied considerably and driven to formation of monoether polyols by adjustment of the ratio of the alkylene oxide to the initiators in the alkoxylation reaction zone. Accordingly, in some implementations, the mixture of alkoxylated polyols will contain at least 10% by weight, preferably at least 20% by weight, more preferably at least about 30% by weight, and even more preferably at least about 40% by weight, based on the total weight of the mixture of alkoxylated polyols, of a monoether polyol. In some implementations, the mixture of alkoxylated polyols will contain from about 10% by weight to about 70% by weight, preferably from about 20% by weight to about 60% by weight, and more preferably from about 30% by weight to about 50% by weight, based on the total weight of the mixture of alkoxylated polyols, of a monoether polyol.

In some implementations, prior to reductive amination, the mixture of alkoxylated polyols may be neutralized with any suitable acid or chemical adsorbent, such as for example, oxalic acid or magnesium silicate, and filtered for the removal of insoluble materials. The mixture of alkoxylated polyols is then charged to a reductive amination zone where it is brought into contact with a reductive amination catalyst, sometimes referred to as a hydrogenation-dehydrogenation catalyst, and reductively aminated in the presence of ammonia and hydrogen under reductive amination conditions. Reductive amination conditions may include, for example, a temperature within the range of about 100° C. to about 240° C. and a pressure within the range of about 500 psi to about 5,000 psi with temperatures within the range of about 180° C. to about 220° C. and pressures within the range of about 1,000 psi to about 2,500 psi being preferred.

Any suitable hydrogenation catalyst may be used, such as those described in U.S. Pat. No. 3,654,370, the contents of which are incorporated herein by reference. In some implementations, the hydrogenation catalyst may comprise one or more of the metals of group VIIIB of the Periodic Table, such as iron, cobalt, nickel, ruthenium, rhodium, palladium, and platinum, mixed with one or more metals of group VIB of the Periodic Table such as chromium, molybdenum or tungsten. A promoter from group IB of the Periodic Table, such as copper, may also be included. As an example, a catalyst may be used comprising from about 60 mole percent to about 85 mole percent of nickel, about 14 mole percent to about 37 mole percent of copper and about 1 mole percent to about 5 mole percent of chromium (as chromia), such as a catalyst of the type disclosed in U.S. Pat. No. 3,152,998. As another example, a catalyst of the type disclosed in U.S. Pat. No. 4,014,933 may be used containing from about 70% by weight to about 95% by weight of a mixture of cobalt and nickel and from about 5% by weight to about 30% by weight of iron. As another example, a catalyst of the type disclosed in U.S. Pat. No. 4,152,353 may be used, comprising nickel, copper and a third component which may be iron, zinc, zirconium or a mixture thereof, for example, a catalyst containing from about 20% by weight to about 49% by weight of nickel, about 36% by weight to about 79% by weight of copper and about 1% by weight to about 15% by weight of iron, zinc, zirconium or a mixture thereof. As still another example, a catalyst of the type described in U.S. Pat. No. 4,766,245 may be used comprising about 60% by weight to about 75% by weight of nickel and about 25% by weight to about 40% by weight of aluminum.

The reductive amination is preferably conducted on a continuous basis with the mixture of alkoxylated polyols, ammonia and hydrogen being continuously charged to a reactor containing a fixed bed of reductive amination catalyst and with the reaction product being continually withdrawn.

The reaction product may be depressured so as to recover excess hydrogen and ammonia for recycle and is then fractionated to remove byproduct water of reaction and to provide the desired etheramine mixture.

In conducting the reductive amination, the reductive amination conditions to be utilized may suitably include the use of from about 4 moles to about 150 moles of ammonia per hydroxyl equivalent of precursor polyol feedstock. Hydrogen is preferably used in an amount ranging from about 0.5 mole equivalents to about 10 mole equivalents of hydrogen per hydroxyl equivalent of alkoxylated polyol feedstock. The contact times within the reaction zone, when the reaction is conducted on a batch basis, may suitably be within the range of from about 0.1 hours to about 6 hours and more preferably from about 0.15 hours to about 2 hours.

When the reaction is conducted on a continuous basis using catalyst pellets, reaction rates may suitably be from about 0.1 grams to about 2 grams of feedstock per hour per cubic centimeter of catalyst and, more preferably, from about 0.3 grams to about 1.6 grams of feedstock per hour per cubic centimeter of catalyst.

Also, the reductive amination may be conducted in the presence of about 1 mole to about 200 moles of ammonia per mole of alkoxylated polyol and more preferably, from about 4 moles to about 130 moles of ammonia per mole of alkoxylated polyol. From about 0.1 moles to about 50 moles of hydrogen per mole of alkoxylated polyol may be employed and, more preferably, from about 1 mole to about 25 moles of hydrogen per mole of alkoxylated polyol.

Some implementations described herein relate to a composition comprising an etheramine of formula (IV):

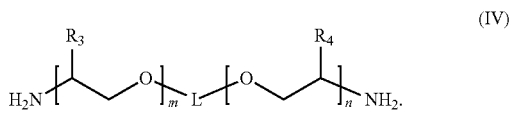

In formula (IV), $R_3$ and $R_4$ may be identical or different and may each be, independently of one another, hydrogen, a linear or branched $C_1$ to $C_5$ alkyl group, a linear or branched $C_2$-$C_5$ alkenyl group, or a substituted or unsubstituted $C_6$-$C_{12}$ aryl group, such as $CH_3$, $C_2H_5$ or $C_6H_5$. m and n may each individually be a non-zero whole number. m and n may each individually be a number from 0 to 6, for example, 0, 1, 2, 3, 4, 5 or 6, wherein at least one of m and n equals 1 or more. m+n may be a number between 1 and 12, for example, 1, 2, 3, 4, 5, 6, 7, 8, 9, 10, 11 or 12.

Some implementations described herein relate to a composition comprising an etheramine of formula (V):

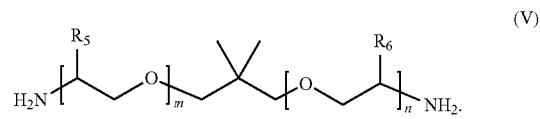

In formula (V), $R_5$ and $R_6$ may be identical or different and may each be, independently of one another, hydrogen, a linear or branched $C_1$ to $C_5$ alkyl group, a linear or branched $C_2$-$C_5$ alkenyl group, or a substituted or unsubstituted $C_6$-$C_{12}$ aryl group, such as $CH_3$, $C_2H_5$ or $C_6H_5$. m and n may each individually be a non-zero whole number. m and n may each individually be a number from 0 to 6, for example, 0, 1, 2, 3, 4, 5 or 6, wherein at least one of m and n equals 1 or more. m+n may be a number between 1 and 12, for example, 1, 2, 3, 4, 5, 6, 7, 8, 9, 10, 11 or 12.

In some implementations, the composition may further comprise at least one of the etheramines of formula (VI), formula (VII) and formula (VIII).

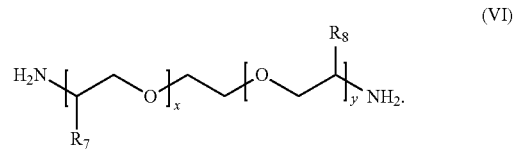

In formula (VI), $R_7$ and $R_8$ may be identical or different and may each be, independently of one another, hydrogen, a linear or branched $C_1$ to $C_5$ alkyl group, a linear or branched $C_2$-$C_5$ alkenyl group, or a substituted or unsubstituted $C_6$-$C_{12}$ aryl group, such as $CH_3$, $C_2H_5$ or $C_6H_5$. x and y may each individually be a number from 0 to 6, for example, 0, 1, 2, 3, 4, 5 or 6, wherein at least one of x and y is 1 or more. x+y may be a number between 1 and 12, for example, 1, 2, 3, 4, 5, 6, 7, 8, 9, 10, 11 or 12.

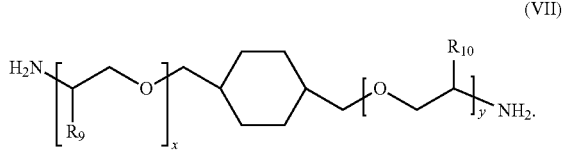

In formula (VII), $R_9$ and $R_{10}$ may be identical or different and may each be, independently of one another, hydrogen, a linear or branched $C_1$ to $C_5$ alkyl group, a linear or branched $C_2$-$C_5$ alkenyl group, or a substituted or unsubstituted $C_6$-$C_{12}$ aryl group, such as $CH_3$, $C_2H_5$ or $C_6H_5$. x and y may each individually be a number from 0 to 6, for example, 0, 1, 2, 3, 4, 5 or 6, wherein at least one of x and y is 1 or more. x+y may be a number between 1 and 12, for example, 1, 2, 3, 4, 5, 6, 7, 8, 9, 10, 11 or 12.

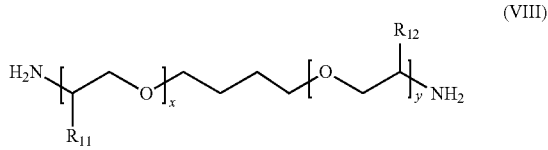

(VIII)

In formula (VIII), $R_{11}$ and $R_{12}$ may be identical or different and may each be, independently of one another, hydrogen, a linear or branched $C_1$ to $C_5$ alkyl group, a linear or branched $C_2$-$C_5$ alkenyl group, or a substituted or unsubstituted $C_6$-$C_{12}$ aryl group, such as $CH_3$, $C_2H_5$ or $C_6H_5$. x and y may each individually be a number from 0 to 6, for example, 0, 1, 2, 3, 4, 5 or 6, wherein at least one of x and y is 1 or more. x+y may be a number between 1 and 12, for example, 1, 2, 3, 4, 5, 6, 7, 8, 9, 10, 11 or 12.

In some implementations, the weight ratio of etheramines derived from the first polyol initiator having a melting point greater than the processing temperature to etheramines derived from the second polyol initiator having a melting point less than the processing temperature is between 30:70 and 90:10. In some implementations, the composition is clear and has a melting point of about 60° C. or less for ease of processing.

According to some implementations, the composition contains at least about 10% by weight, at least about 20% by weight, at least about 30% by weight, at least about 40% by weight, at least about 50% by weight, at least about 60% by weight, at least about 70% by weight, at least about 80% by weight, or at least about 90% by weight of etheramines derived from the first polyol initiator having a melting point greater than the processing temperature based on the total weight of the etheramine mixture. In other implementations, the etheramine mixture contains from about 10% by weight to about 90% by weight, from about 20% by weight to about 80% by weight, or from about 30% by weight to about 70% by weight of the etheramines derived from the first polyol initiator having a melting point greater than the processing temperature based on the total weight of the etheramine mixture.

In some implementations, the composition comprises from about 10% by weight to about 90% by weight of the etheramines derived from the first polyol initiator having a melting point greater than the processing temperature based on the total weight of the etheramine mixture and from about 90% by weight to about 10% by weight of the ethereamines derived from the second polyol initiator having a melting point less than the processing temperature based on the total weight of the etheramine mixture.

In still yet another implementation, the present disclosure generally provides compositions comprising and processes for producing a polyurea material by reacting the etheramine mixture described herein with an organic polyisocyanate.

In still yet another implementation, the present disclosure generally provides compositions and processes for producing an epoxy resin system by contacting the etheramine mixture with an epoxy resin to form an epoxy resin system and curing the epoxy resin system.

Due to its favorable properties, the etheramine mixture described herein may be used as a constituent in a formulation which finds use in a wide variety of industrial applications, for example for the production of moldings (casting resins), fiber-reinforced composites, such as wind turbine generator blades, for tool manufacture or for the production of coatings and/or intermediate coatings on a wide variety of substrates, for example on substrates of an organic or inorganic nature, such as wood, wood fibers (wood sealing), textiles of natural or synthetic origin, plastics, glass, ceramics, building materials, such as concrete, fiberboard, and artificial stone, on metal, such as iron, aluminum, copper and the like. In addition, the etheramine mixture described herein can be employed as a constituent of adhesives, cement, laminating resin, synthetic resin cement, paint or coating. The formulation can be prepared prior to or during use by contacting the constituents, for example by mixing, and it can also be applied to any type of surface(s), for example, by brushing, spraying, dipping coating, extruding, printing, electrostatic spraying, and the like, and then subsequently cured to form a cured material.

According to one implementation, the etheramine mixture of the present disclosure is contacted with an epoxy resin to form an epoxy resin formulation. The epoxy resin formulation may then be subjected to conditions sufficient to cause the epoxy resin formulation to cure.

The epoxy resin may be any one or mixture of reactive epoxy resin(s) having a 1,2-epoxy equivalency (functionality), on the average, of at least 1 epoxide groups per molecule, preferably at least 1.3 epoxide groups per molecule, and more preferably at least 1.6 epoxide groups per molecule, and even more preferably with epoxy resins having a functionality of at least 2 epoxy groups per molecule such that the mixture will polymerize to form a useful material with the amine described herein or its blend with other amine hardeners. In another implementation, the epoxy resin has a functionality on the average ranging from at least 1.3 epoxide groups per molecule to about 8 epoxide groups per molecule, preferably from at least about 1.6 epoxide groups per molecule to about 5 epoxide groups per molecule. The epoxy resin can be saturated or unsaturated, linear or branched, aliphatic, cycloaliphatic, aromatic or heterocyclic, and may bear substituents such as bromine or fluorine. It may be monomeric or polymeric, liquid or solid, but is preferably liquid or a low melting solid at room temperature.

According to one implementation, the epoxy resin is a polyglycidyl epoxy compound, such as a polyglycidyl ether, poly(β-methylglycidyl) ether, polyglycidyl ester or poly(β-methylglycidyl) ester. The synthesis and examples of polyglycidyl ethers, poly(β-methylglycidyl) ethers, polyglycidyl esters and poly(β-methylglycidyl) esters are disclosed in U.S. Pat. No. 5,972,563, which is incorporated herein by reference. For example, ethers may be obtained by reacting a compound having at least one free alcoholic hydroxyl group and/or phenolic hydroxyl group with a suitably substituted epichlorohydrin under alkaline conditions or in the presence of an acidic catalyst followed by alkali treatment. The alcohols may be, for example, acyclic alcohols, such as ethylene glycol, diethylene glycol and higher poly(oxyethylene) glycols, propane-1,2-diol, or poly(oxypropylene) glycols, propane-1,3-diol, butane-1,4-diol, poly(oxytetramethylene) glycols, pentane-1,5-diol, hexane-1,6-diol, hexane-2,4,6-triol, glycerol-1,1,1-trimethylolpropane, bistrimethylolpropane, pentaerythritol and sorbitol. Suitable glycidyl ethers may also be obtained, however, from cycloaliphatic alcohols, such as 1,3- or 1,4-dihydroxycyclohexane, bis(4-hydroxycyclo-hexyl)methane, 2,2-bis(4-hydroxycyclohexyl)propane or 1,1-bis(hydroxymethyl)cyclohex-3-ene, or they may possess aromatic rings, such as N,N-bis(2-hydroxyethyl)aniline or p,p'-bis(2-hydroxyethylamino) diphenylmethane.

Representative examples of polyglycidyl ethers or poly(β-methylglycidyl) ethers include those based on monocyclic phenols, for example, on resorcinol or hydroquinone, on polycyclic phenols, for example, on bis(4-hydroxyphenyl) methane (Bisphenol F), 2,2-bis(4-hydroxyphenyl)propane (Bisphenol A), bis(4-hydroxyphenyl)S (Bisphenol S), alkoxylated Bisphenol A, F or S, triol extended Bisphenol A, F or S and brominated Bisphenols A, F or S, hydrogenated Bisphenol A, F or S, glycidyl ethers of phenols and phenols with pendant groups or chains, on condensation products, obtained under acidic conditions, of phenols or cresols with formaldehyde, such as phenol novolaks and cresol novolaks, or on siloxane diglycidyls.

Polyglycidyl esters and poly(β-methylglycidyl) esters may be produced by reacting epichlorohydrin or glycerol dichlorohydrin or β-methylepichlorohydrin with a polycarboxylic acid compound. The reaction is expediently carried out in the presence of bases. The polycarboxylic acid compounds may be, for example, glutaric acid, adipic acid, pimelic acid, suberic acid, azelaic acid, sebacic acid or dimerized or trimerized linoleic acid. Likewise, however, it is also possible to employ cycloaliphatic polycarboxylic acids, for example tetrahydrophthalic acid, 4-methyltetrahydrophthalic acid, hexahydrophthalic acid or 4-methylhexahydrophthalic acid. It is also possible to use aromatic polycarboxylic acids such as, for example, phthalic acid, isophthalic acid, trimellitic acid or pyromellitic acid, or else carboxyl-terminated adducts, for example of trimellitic acid and polyols, for example glycerol or 2,2-bis(4-hydroxycyclohexyl)propane, can be used.

In another implementation, the epoxy resin is a non-glycidyl epoxy compound. Non-glycidyl epoxy compounds may be linear, branched, or cyclic in structure. For example, there may be included one or more epoxide compounds in which the epoxide groups form part of an alicyclic or heterocyclic ring system. Others include an epoxy-containing compound with at least one epoxycyclohexyl group that is bonded directly or indirectly to a group containing at least one silicon atom. Examples are disclosed in U.S. Pat. No. 5,639,413, which is incorporated herein by reference. Still others include epoxides which contain one or more cyclohexene oxide groups and epoxides which contain one or more cyclopentene oxide groups. Particularly suitable non-glycidyl epoxy compound's include the following difunctional non-glycidyl epoxide compounds in which the epoxide groups form part of an alicyclic or heterocyclic ring system: bis(2,3-epoxycyclopentyl) ether, 1,2-bis(2,3-epoxycyclopentyloxy)ethane, 3,4-epoxycyclohexyl-methyl, 3,4-epoxycyclohexanecarboxylate, 3,4-epoxy-6-methyl-cyclohexylmethyl 3,4-epoxy-6-methylcyclohexanecarboxylate, di(3,4-epoxycyclohexylmethyl)hexanedioate, di(3,4-epoxy-6-methylcyclohexylmethyl) hexanedioate, ethylenebis(3,4-epoxycyclohexanecarboxylate), ethanediol di(3,4-epoxycyclohexylmethyl)ether, vinylcyclohexene dioxide, dicyclopentadiene diepoxide or 2-(3,4-epoxycyclohexyl-5,5-spiro-3,4-epoxy)cyclohexane-1,3-dioxane, and 2,2'-bis-(3,4-epoxy-cyclohexyl)-propane.

In another implementation, the epoxy resin is an epoxy novolac compound obtained by the reaction of, preferably in the presence of a basic catalyst such as sodium or potassium hydroxide, an epihalohydrin, such as epichlorohydrin, with a resinous condensate of an aldehyde, such as formaldehyde and either a monohydric phenol or polyhydric phenol.

In other implementations, the epoxy resin is a poly(N-glycidyl) compound or poly(S-glycidyl) compound. Poly(N-glycidyl) compounds are obtainable, for example, by dehydrochlorination of the reaction products of epichlorohydrin with amines containing at least two amine hydrogen atoms. These amines may be, for example, n-butylamine, aniline, toluidine, m-xylylenediamine, bis(4-aminophenyl)methane or bis(4-methylaminophenyl)methane. Other examples of poly(N-glycidyl) compounds include N,N'-diglycidyl derivatives of cycloalkyleneureas, such as ethyleneurea or 1,3-propyleneurea, and N,N'-diglycidyl derivatives of hydantoins, such as of 5,5-dimethylhydantoin. Examples of poly(S-glycidyl) compounds are di-S-glycidyl derivatives derived from dithiols, for example ethane-1,2-dithiol or bis(4-mercaptomethylphenyl) ether.

It is also possible to employ epoxy-containing compounds in which the 1,2-epoxide groups are attached to different heteroatoms or functional groups. Examples of these compounds include the N,N,O-triglycidyl derivative of 4-aminophenol, the glycidyl ether/glycidyl ester of salicylic acid, N-glycidyl-N'-(2-glycidyloxypropyl)-5,5-dimethylhydantoin or 2-glycidyloxy-1,3-bis(5,5-dimethyl-1-glycidylhydantoin-3-yl)propane.

Other epoxide derivatives may be employed, such as vinyl cyclohexene dioxide, limonene dioxide, limonene monoxide, vinyl cyclohexene monoxide, 3,4-epoxycyclohexlmethyl acrylate, 3,4-epoxy-6-methyl cyclohexylmethyl 9,10-epoxystearate, and 1,2-bis(2,3-epoxy-2-methylpropoxy)ethane. Also conceivable is the use of oxetanes or liquid pre-reacted adducts of epoxy-containing compounds, such as those mentioned above, with hardeners for the epoxy resins.

The epoxy resin formulation may further contain customary additives and auxiliaries such as stabilizers, modifiers, antifoaming agents, toughening agents, accelerators, co-curing agents, leveling agents, thickening agents, flame retardants, antioxidants, pigments, dyes, fillers, and combinations thereof. For example, an accelerator such as guanidine or a derivative thereof may be used in the epoxy resin formulation. Examples of guanidine derivatives include without limitation, an alkylguanidine such as dimethylguanidine or tetramethyl guanidine, or a guanidinium salt derived from any of these. Examples of guanidinium salts include without limitation, guanidine carbonates, guanidine acetates, and guanidine nitrates. One skilled in the art with the benefit of this disclosure will recognize appropriate additives and auxiliaries for use in the implementations described herein.

In some implementations described herein, the ether-amine mixtures may not require the use of co-curing agent, such as cycloaliphatic diamines such as isophorone diamine. In these implementations, fewer materials would be needed to manufacture the epoxy resin as well as less energy needed to reach the lower cure temperature.

Once formulated, the epoxy resin formulation may be applied to one or more surfaces, for example, brushing, spraying, dipping, electrostatic spraying, etc., and subjected to conditions suitable to cause the epoxy resin system to cure. In one implementation, the epoxy resin formulation is cured at ambient conditions. In another implementation, the epoxy resin formulation is cured at an elevated temperature such as, at a temperature within the range from about 40° C. to about 220° C. In some implementations of the present disclosure, a lower cure temperature and/or lower cure time may be needed to reach desired cure properties, such as glass transition temperatures, than is typically required in current epoxy resin systems. Achieving improved cure property development at lower curing (such as baking) temperatures and/or shorter curing times means a potential savings in energy costs and a possible reduction in manufacturing process time (increased productivity). In implementations of the present disclosure, the temperature used in curing may be about, or less than, 40° C., 45° C., 50° C., 55° C., 60° C.

and 65° C. In implementations of the present disclosure, the cure time may be from about 2 hours (hrs) to about 6 hrs, including the intervals of about 2.5 hrs, 3 hrs, 3.5 hrs, 4 hrs, 4.5 hrs, 5 hrs and 5.5 hrs. In an implementation of the present disclosure, the epoxy resin system is cured from about 3 to about 6 hours at about 55° C. One skilled in the art will recognize, with the benefit of this disclosure, how to reach desired cure properties using lower temperatures and/or lower cure times.

In still another implementation, the etheramine mixture of the present disclosure is reacted with an organic polyisocyanate to form a polyurea. The organic polyisocyanate includes standard isocyanate compounds and compositions known to those skilled in the art. Preferred examples include MDI-based quasi prepolymers such as those commercially available as RUBINATE® 9480, RUBINATE® 9484, and RUBINATE® 9495 brand products which are all available from Huntsman International, LLC. Liquefied MDI such as MONDUR® ML isocyanate, available from Bayer MaterialScience, may also be used as all or part of the isocyanate.

Other organic polyisocyanates which can be employed include those generally known to one skilled in the art. Thus, for instance, they can include aliphatic isocyanates of the type described in U.S. Pat. No. 4,748,192. Accordingly, they are typically aliphatic diisocyanates and, more particularly, are the trimerized or the biuretic form of an aliphatic diisocyanate, such as hexamethylene diisocyanate, or the bifunctional monomer of the tetraalkyl xylene diisocyanate, such as the tetramethyl xylene diisocyanate. Another example of an aliphatic isocyanate is cyclohexane diisocyanate. Other useful aliphatic isocyanates are described in U.S. Pat. No. 4,705,814 which is fully incorporated herein by reference. They include aliphatic diisocyanates, for example, alkylene diisocyanates with 4 to 12 carbon atoms in the alkylene radical, such as 1,12-dodecane diisocyanate and 1,4-tetramethylene diisocyanate. Also described are cycloaliphatic diisocyanates, such as 1,3 and 1,4-cyclohexane diisocyanate as well as any desired mixture of these isomers, 1-isocyanato-3,3,5-trimethyl-5-isocyanato methylcyclohexane (isophorone diisocyanate); 4,4'-,2,2'- and 2,4'-dicyclohexylmethane diisocyanate as well as the corresponding isomer mixtures, and the like.

A wide variety of aromatic polyisocyanates may also be used to form the polyurea of the present disclosure. Typical aromatic polyisocyanates include p-phenylene diisocyanate, polymethylene polyphenylisocyanate, 2,6-toluene diisocyanate, dianisidine diisocyanate, bitolylene diisocyanate, naphthalene-1,4-diisocyanate, bis(4-isocyanatophenyl)methane, bis(3-methyl-3-iso-cyanatophenyl)methane, bis(3-methyl-4-isocyanatophenyl)methane, and 4,4'-diphenylpropane diisocyanate. Other aromatic polyisocyanates which may be used are methylene-bridged polyphenyl polyisocyanate mixtures which have a functionality of from about 2 to about 4. These latter isocyanate compounds are generally produced by the phosgenation of corresponding methylene bridged polyphenyl polyamines, which are conventionally produced by the reaction of formaldehyde and primary aromatic amines, such as aniline, in the presence of hydrochloric acid and/or other acidic catalysts. Known processes for preparing polyamines and corresponding methylene-bridged polyphenyl polyisocyanates therefrom are described in the literature and in many patents, for example, U.S. Pat. Nos. 2,683,730; 2,950,263; 3,012,008; 3,344,162 and 3,362,979, all of which are fully incorporated herein by reference. Usually, methylene-bridged polyphenyl polyisocyanate mixtures contain about 20 to about 100 weight percent methylene diphenyl diisocyanate isomers, with the remainder being polymethylene polyphenyl diisocyanates having higher functionalities and higher molecular weights. Typical of these are polyphenyl polyisocyanate mixtures containing about 20 to about 100 weight percent diphenyl diisocyanate isomers, of which about 20 to about 95 weight percent thereof is the 4,4'-isomer with the remainder being polymethylene polyphenyl polyisocyanates of higher molecular weight and functionality that have an average functionality of from about 2.1 to about 3.5. These isocyanate mixtures are known, commercially available materials and can be prepared by the process described in U.S. Pat. No. 3,362,979. A preferred aromatic polyisocyanate is methylene bis (4-phenylisocyanate) or "MDI". Pure MDI, quasi-prepolymers of MDI, modified pure MDI, etc. are useful to prepare a polyurea according to the invention. Since pure MDI is a solid and, thus, often inconvenient to use, liquid products based on MDI or methylene bis(4-phenylisocyanate) are used herein. U.S. Pat. No. 3,394,164, incorporated herein by reference, describes a liquid MI product. More generally, uretonimine modified pure MDI is included also. This product is made by heating pure distilled MDI in the presence of a catalyst. The liquid product is a mixture of pure MDI and modified MDI. The term organic polyisocyanate also includes quasi-prepolymers of isocyanates or polyisocyanates with active hydrogen containing materials.

EXAMPLES

The following non-limiting examples are provided to further illustrate embodiments described herein. However, the examples are not intended to be all inclusive and are not intended to limit the scope of the embodiments described herein.

Example 1

To a dry, nitrogen purged reactor were added 3175 grams of neopentyl glycol, 794 grams of ethylene glycol and 14.85 grams of KOH flake. Then, 5186 grams of 1,2-butyleneoxide was slowly added to the diol mixture while agitating. The reactor was then heated to 125° C. and temperature control was initiated. The reactor was then held at 125° C. for several hours. The diol mixture was then digested down to constant pressure. Unreacted oxide was stripped out. Then an amount of DI water and magnesium silicate (i.e., Magnesol®) was added to the diol mixture and digested for 2 hours at 120° C. The reaction mixture was then stripped at 50 mm Hg for about one hour to remove any light reactants and water and the filtered product was then collected. The final alkoxylated polyol mixture had a hydroxyl number of 523 and a water content of <0.01%. The average molecular weight of the final alkoxylated polyol mixture was 215.

Example 2

To a dry, nitrogen purged reactor were added 3175 grams of neopentyl glycol, 794 grams of ethylene glycol and 13.21 grams of KOH flake. Then, 4173 grams of propyleneoxide was slowly added to the diol mixture while agitating. The reactor was then heated to 120° C. and temperature control was initiated. The reactor was then held at 120° C. for several hours. The diol mixture was then digested down to constant pressure. Unreacted oxide was stripped out. Then an amount of DI water and magnesium silicate (i.e., Magnesol®) was added to the diol mixture and digested for 2 hours at 120° C. The reaction mixture was then stripped at 50 mm Hg for about one hour to remove any light reactants and water and the filtered product was then collected. The final alkoxylated polyol mixture had a hydroxyl number of 571 and a water content of about 0.08%. The average molecular weight of the final alkoxylated polyol mixture was 197.

Example 3

To a dry, nitrogen purged reactor were added 3402 grams of neopentyl glycol, 1458 gram of 1,4 butanediol and 14.28 grams of KOH flake. Then, 3939 grams of propyleneoxide was slowly added to the diol mixture while agitating. The reactor was then heated to 120° C. and temperature control was initiated. The reactor was then held at 120° C. for several hours. The diol mixture was then digested down to constant pressure. Unreacted oxide was stripped out. Then an amount of DI water and magnesium silicate (i.e., Magnesol®) was added to the diol mixture and digested for 2 hours at 120° C. The reaction mixture was then stripped at 50 mm Hg for about one hour to remove any light reactants and water and the filtered product was then collected. The final alkoxylated polyol mixture had a hydroxyl number of 631 and a water content of 0.05%. The average molecular weight of the final alkoxylated polyol mixture was 178.

Example 4

To a dry, nitrogen purged reactor were added 3175 grams of neopentyl glycol, 1361 grams of cyclohexane dimethanol and 12.95 grams of KOH flake. Then, 3447 grams of propyleneoxide was slowly added to the diol mixture while agitating. The reactor was then heated to 120° C. and temperature control was initiated. The reactor was then held at 120° C. for several hours. The diol mixture was then digested down to constant pressure. Unreacted oxide was stripped out. Then an amount of DI water and magnesium silicate (i.e., Magnesol®) was added to the diol mixture and digested for 2 hours at 120° C. The reaction mixture was then stripped at 50 mm Hg for about one hour to remove any light reactants and water and the filtered product was then collected. The final alkoxylated polyol mixture had a hydroxyl number of 560 and a water content of <0.01%. The average molecular weight of the final alkoxylated polyol mixture was 200.

The alkoxylated polyol mixtures mentioned above were then each reductively aminated with ammonia to prepare the corresponding amines in a 100 cc continuous unit with a fixed-bed nickel based catalyst. The polyol and ammonia were pumped separately, mixed in-line with hydrogen and fed through the catalyst bed. The polyol and ammonia were kept in an approximate 1:1 weight feed ratio, while the ammonia to hydrogen mole ratio was kept at about 10-20:1 weight feed ratio. The reactor pressure was held at 2,000 psig and the temperature was maintained at about 180-220° C. for the entire reductive amination step. The polyol and ammonia feed rates used in each run varied between about 65 g/hr to 100 g/hr. The products were collected and stripped of excess ammonia, water and light amines.

Table 1 depicts the melting behavior of selected alcohol mixtures, each mixture includes low and high melting point alcohols mixed to form a low melting point mixture for ease of processing.

TABLE 1

|  | Weight ratio | Room Temperature | 50° C. | 60° C. |
|---|---|---|---|---|
| Neopentyl glycol/ Ethylene glycol | 80/20 | Solid/liquid | Clear liquid | Clear liquid |
|  | 70/30 | Waxy solid | Clear liquid | Clear liquid |
|  | 60/40 | Liquid with crystal | — | Clear liquid |
| Neopentyl glycol/ Cyclohexane dimethanol | 80/20 | Solid | Solid | Waxy solid |
|  | 75/25 | Solid | — | Viscous hazy liquid |
|  | 70/30 | — | Slightly hazy liquid | Clear liquid |
| Neopentyl glycol/ 1,4-Butane diol | 80/20 | Solid/liquid | Solid/liquid | Solid/liquid |
|  | 70/30 | Waxy solid | Clear liquid | Clear liquid |
|  | 60/40 | Liquid with crystal | — | Clear liquid |

Example 5

An epoxy resin formulation containing a bisphenol NF based epoxy resin having an epoxy equivalent weight of 169 was cured using the etheramine mixtures of Examples 1-4 as well as by commercially available curing agents (JEFFAMINE® D-230 amine). The epoxy resin and amine curing agent were mixed in the amounts listed below in Table 2 to form epoxy system formulations and then cured under the conditions listed in Table 2. The glass transition temperature ($T_g$) of the cured material was then measured using a differential scanning calorimeter (DSC) and choosing the temperature at the inflection point of the heat capacity change as the $T_g$. The results are presented below in Table 2. In general high melting point alcohols have rigid or hindered structure, which leads to enhanced thermal or mechanical properties. Based on the art of this patent, high melting point alcohol raw materials could be processed under low temperature for energy saving and property improvement.

TABLE 2

|  | Formulation A | Formulation B | Formulation C | Formulation D | Formulation E |
|---|---|---|---|---|---|
| Part A |  |  |  |  |  |
| Diluted epoxy resin | 100 pbw | 100 pbw | 100 pbw | 100 pbw | 100 pbw |
| Part B |  |  |  |  |  |
| Example 1 | 36 |  |  |  |  |
| Example 2 |  | 33 |  |  |  |
| Example 3 |  |  | 29 |  |  |
| Example 4 |  |  |  | 34 |  |
| JEFFAMINE ® D-230 amine |  |  |  |  | 36 |
| $T_g$, ° C., after 6 hours at 80° C. | 64 | 71 | 66 | 75 | 70 |
| $T_g$, ° C., after 6 hours at 80° C. (2nd Scan) | 69 | 70 | 68 | 79 | 74 |

While the foregoing is directed to embodiments of the present invention, other and further embodiments of the invention may be devised without departing from the basic scope thereof, and the scope thereof is determined by the claims that follow.

The invention claimed is:

1. A process for preparing an etheramine mixture, comprising:
   (a) mixing a first polyol initiator having a melting point greater than a processing temperature and a second polyol initiator having a melting point less than the processing temperature to form a polyol initiator mixture having a melting point less than the processing temperature;
   (b) charging the polyol initiator mixture to an alkoxylation reaction zone in the presence of an alkali metal hydroxide catalyst;
   (c) contacting the polyol initiator mixture with an alkylene oxide in the alkoxylation reaction zone at conditions sufficient to provide a mixture of alkoxylated precursor polyols comprising at least 10% by weight of a monoether polyol based on the total weight of the mixture of alkoxylated precursor polyols; and
   (d) charging the mixture of alkoxylated precursor polyols to a reductive amination zone and reductively aminating the mixture of alkoxylated precursor polyols in the presence of a reductive amination catalyst and ammonia to form an etheramine mixture comprising:
      (i) at least one etheramine selected from the following formulas:

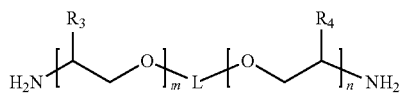

wherein L is a linear or branched $C_2$-$C_{18}$ alkykene; $C_3$-$C_{12}$ cycloalkylene; $C_2$-$C_4$ alkylene-$C_3$-$C_{12}$ cycloalkylene or $C_2$-$C_8$ alkylene-$C_3$-$C_{12}$ cycloalkylene-$C_2$-$C_4$ alkylene;
wherein $R_3$ and $R_4$ may be identical or different and may each be, independently of one another, hydrogen, a linear or branched $C_1$ to $C_5$ alkyl group, a linear or branched $C_2$-$C_5$ alkenyl group, or a substituted or unsubstituted $C_6$-$C_{12}$ aryl group; and
wherein m and n may each individually be a number from 0 to 6 wherein at least one of m and n is 1 or more, and

wherein $R_5$ and $R_6$ are identical or different and are each, independently of one another, hydrogen, a linear or branched $C_1$ to $C_5$ alkyl group, a linear or branched $C_2$-$C_5$ alkenyl group, or a substituted or unsubstituted $C_6$-$C_{12}$ aryl group and m+n equals a non-zero whole number between one and six; and
   (ii) at least one etheramine selected from the following formula:

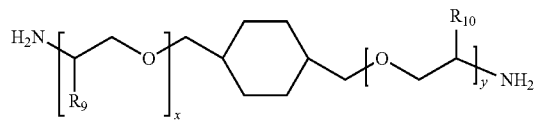

wherein $R_9$ and $R_{10}$ are identical or different and are each, independently of one another, hydrogen, a linear or branched $C_1$ to $C_5$ alkyl group, a linear or branched $C_2$-$C_5$ alkenyl group, or a substituted or unsubstituted $C_6$-$C_{12}$ aryl group and x+y equals a non-zero whole number between one and six; and
wherein the etheramine mixture has a weight ratio of etheramines derived from the first polyol initiator to etheramines derived from the second polyol initiator between 30:70 to 90:10 and the processing temperature is greater than 60° C.

2. The process of claim 1, wherein the first polyol initiator is neopentyl glycol and optionally, at least one of 1,4-butanediol and ethylene glycol.

3. The process of claim 2, wherein the second polyol initiator comprises 1,4-cyclohexanedimethanol.

4. The process of claim 2, wherein the alkylene oxide is selected from the group consisting of: propylene oxide, butylene oxide, ethylene oxide and combinations thereof.

5. The process of claim 1, wherein the melting point of the first polyol initiator is greater than 100° C.

6. The process of claim 1, further comprising:
   (e) contacting the etheramine mixture with an epoxy resin to form an epoxy resin system; and
   (f) curing the epoxy resin system.

7. The process of claim 1, further comprising:
   (e) reacting the etheramine mixture with an organic polyisocyanate to produce a polyurea.

8. The process of claim 1, wherein the first polyol initiator is a solid at the processing temperature and the second polyol initiator is a liquid at the processing temperature.

9. The process of claim 8, wherein the polyol initiator mixture is a liquid at the processing temperature.

10. The process of claim 1, further comprising a step after step (c) and before step (d) whereby the mixture of alkoxylated precursor polyols are neutralized with an acid or a chemical adsorbent and then filtered to remove at least a portion of any insoluble materials from the mixture of alkoxylated precursor polyols.

* * * * *